(12) United States Patent
Barnea et al.

(10) Patent No.: US 7,476,649 B2
(45) Date of Patent: Jan. 13, 2009

(54) ANTIPROLIFERATIVE AND ANTIVIRAL PROTEINS AND PEPTIDES

(75) Inventors: Eytan R. Barnea, Cherry Hill, NJ (US); Paul C. Leavis, Eppins, NH (US)

(73) Assignee: Biospectrum, Inc., Cherry Hill, NJ (US)

( * ) Notice: Subject to any disclaimer, the term of this patent is extended or adjusted under 35 U.S.C. 154(b) by 405 days.

(21) Appl. No.: 10/670,490

(22) Filed: Sep. 25, 2003

(65) Prior Publication Data
US 2004/0043936 A1    Mar. 4, 2004

Related U.S. Application Data

(63) Continuation of application No. 09/720,693, filed as application No. PCT/US99/14834 on Jun. 30, 1999, now abandoned.

(60) Provisional application No. 60/091,579, filed on Jul. 2, 1998, provisional application No. 60/119,264, filed on Feb. 9, 1999.

(51) Int. Cl.
*A61K 38/00* (2006.01)
*A61K 38/08* (2006.01)
*C07K 7/06* (2006.01)
*C07K 14/00* (2006.01)

(52) U.S. Cl. .............. 514/2; 514/16; 514/21; 530/300; 530/329

(58) Field of Classification Search ............... None
See application file for complete search history.

(56) References Cited

U.S. PATENT DOCUMENTS 5,393,534 A    2/1995   Cavanaugh et al.
5,648,340 A    7/1997   Barnea
5,658,792 A    8/1997   Nuell et al.

FOREIGN PATENT DOCUMENTS

| WO | WO 92/09294 A | 6/1992 |
| WO | WO98/52550 | * 11/1998 |
| WO | WO0240717 | * 5/2002 |

OTHER PUBLICATIONS

Abstract of Brill et al, Proceedings of the Society for Experimental Biology and Medicine, 1993, vol. 204, pp. 261-269).*
Abstract of Ajinomotot (Biotech on STN, The Thomson Corp), JP 60178820, Sep. 12, 1985).*
Johnson and Tracey, 'Peptide and Protein Drug Delivery', In: Encyclopedia of Controlled Drug Delivery, vol. 2, 1999, pp. 816-833.*
Barnea, E.R. et al., *Control of cell proliferation by embryonal-origin factos*, American Journal of Reproductive Immunology, 1996, 35(4), pp. 318-324.
Fresney et al, The Culture of Animal Cells, 1994, page 5.
Gura (Science, 1997, 278: 1041-1042).
Geetha Devi et al (Biochemistry and Cell biology, 1993, vol. 71, pp. 241-247).
Chapekar et al (Experimental Cell Research, 1989, vol. 185, pp. 247-257).
Jain (Sci. Am., 1994, 271:58-65).
Curti (Crit. Rev. in Oncology/Hematology, 1993, 14:29-39).
Mashima et al. (Journal of Biochemistry, 1988, vol. 103, pp. 1020-1026).
Huggett et al. (Journal of Cellular Biochemistry, 35:305-314 (1987).

* cited by examiner

*Primary Examiner*—Karen A Canella
(74) *Attorney, Agent, or Firm*—Pepper Hamilton LLP

(57) ABSTRACT

The present invention relates to peptides and proteins which may be used to inhibit infection or cell proliferation. It is based, at least in part, on the discovery of peptides and proteins isolated from embryonic tissue which have been found to exhibit an antiproliferative effect on a variety of cancer cells and/or to act as broad-spectrum antiviral agents.

6 Claims, 10 Drawing Sheets

Figure 1:
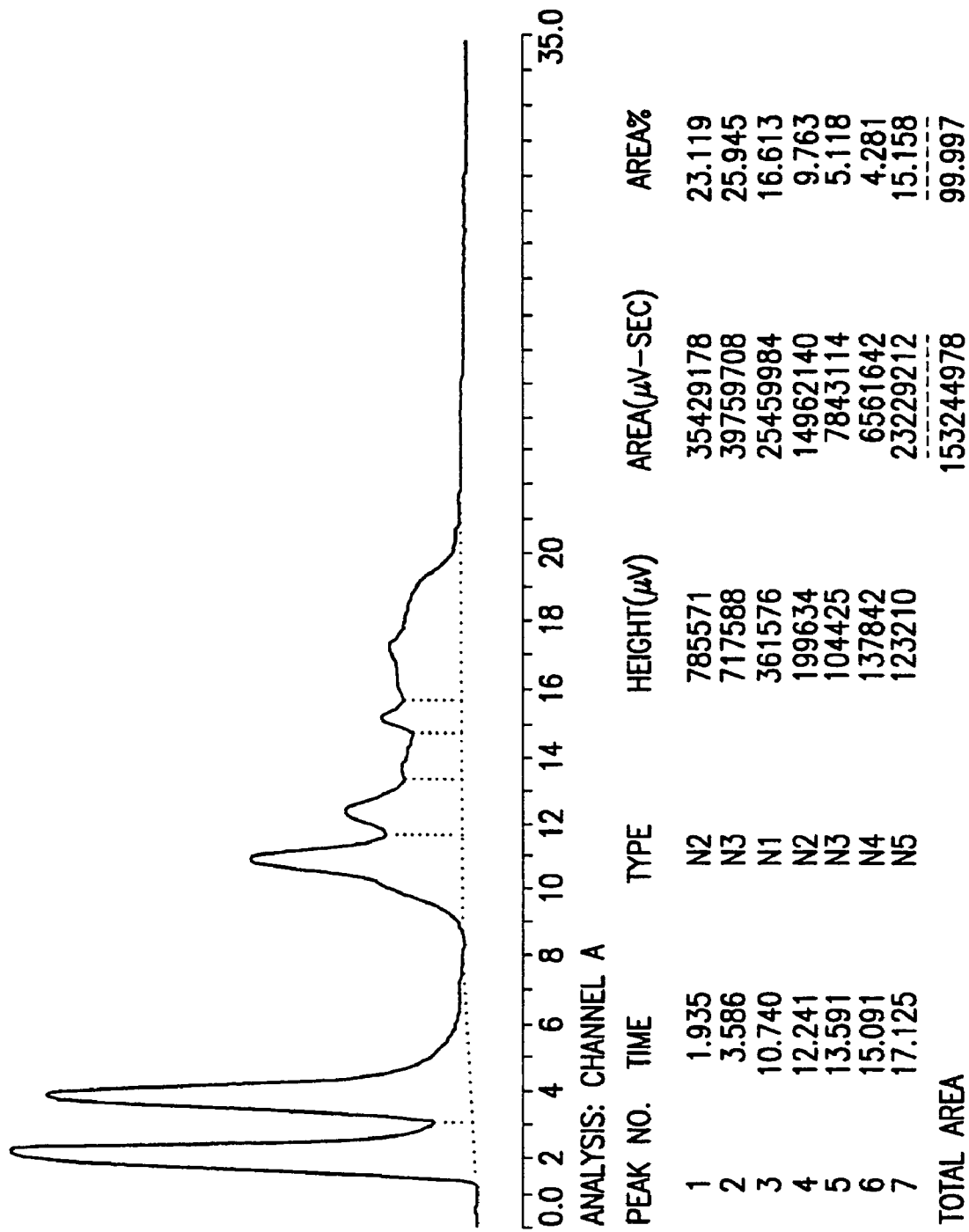

A= Highly Concentrated DPs
B= Molecular Weight Standards

US 7,476,649 B2

ANTIPROLIFERATIVE AND ANTIVIRAL PROTEINS AND PEPTIDES

CROSS REFERENCES TO RELATED APPLICATIONS

This application claims priority to, and is a continuation of, the U.S. patent application Ser. No. 09/720,693 filed Feb. 21, 2001 now abandoned, which is a national stage filing of International Patent Application PCT/US99/14834 filed Jun. 30, 1999 which claims priority from U.S. Provisional Patents 60/091,579 and 60/119,264, filed Jul. 2, 1998 and Feb. 9, 1999, respectively.

1. INTRODUCTION

The present invention relates to peptides and proteins which may be used to inhibit infection or cell proliferation. It is based, at least in part, on the discovery of peptides and proteins isolated from embryonic tissue which have been found to exhibit an antiproliferative effect on a variety of cancer cells and/or to act as broad-spectrum antiviral agents.

2. BACKGROUND OF THE INVENTION

The present invention relates to proteins and peptides which have antiproliferative and/or anti-infective activity. These molecules have been isolated and characterized as part of a research initiative to identify factors responsible for the delicate balance between proliferative and antiproliferative forces which operate during embryogenesis. The research has been based on the theory that pregnancy operates, figuratively speaking, like a reversible cancer, in that like cancer, the products of conception are invasive and penetrate the circulation. Embryonic cells, and their tumor cell counterparts, express similar surface antigens (e.g., alphafetoprotein and carcinoembryonic antigen) and secreted factors. Furthermore, the conceptus, like a tumor, is not rejected by the mother's body, but rather harnesses maternal resources to secure its well-being. Unlike cancer, however, the invasiveness and tolerance associated with pregnancy are reversible at almost any time.

As described in U.S. Pat. No. 5,648,340 by Dr. Barnea, which is incorporated by reference in its entirety herein, agents have been identified which operate to control the development of the embryo such that proliferation, invasiveness and differentiation may occur without substantially injuring the maternal host. It has been discovered that several agents produced by the embryo appear to play an important role in its development. U.S. Pat. No. 5,648,340 discloses the purification of protein extracts having molecular weights less than 10,000 daltons (and particularly less than 8,000 daltons) which have antiproliferative activity and less than 3,000 daltons which exhibit proliferative activity.

The protein preparations described in U.S. Pat. No. 5,648,340 have now been subjected to further analysis, and it has been discovered that proteins from high molecular weight fractions of the extract exhibit both an antiproliferative effect on cancer cells and a broad-spectrum antiviral effect, and that low molecular weight fractions of the extract comprise an active antiproliferative agent which is a heptapeptide having a molecular weight of approximately 820 daltons.

In particular, according to the present invention, the higher molecular weight subfractions of the proteins described in U.S. Pat. No. 5,648,340 were observed to inhibit the proliferation of various types of cancer cells and also the cytopathic effect of a variety of viruses, including viruses of the Retrovirus, Bunyavirus, Togavirus, Reovirus, Herpesvirus, and Poxvirus families. These viruses are structurally extremely diverse and exert their effects through distinct biological mechanisms.

Retroviruses, such as human immunodeficiency viruses types 1 and 2, are RNA viruses which reverse-transcribe their genomic RNA as part of their replicative cycle. In DNA ("provirus") form, they are able to integrate into host chromosomal DNA, where they can persist for extended periods of time. Bunyaviruses are arthropod-borne viruses which use negative strand RNA as their genetic material. Examples of members of the Bunyaviridae family are Bunyamwera, Uukuniemi, La Crosse, Punta Toro, and San Angelo viruses, and Rift Valley, Sandfly, and Crimean-Congo hemorrhagic fever viruses. Togaviruses are icosahedral, positive-strand RNA viruses, and include numerous viruses which are pathogenic in man. Among the Togaviruses are eastern equine encephalitis, western equine encephalitis, Venezuelan equine encephalitis, Sindbis, Chikungunya, Semiliki Forest, St. Louis encephalitis, yellow fever, rubella, and dengue viruses. Reoviruses are double-stranded RNA viruses which are frequently associated with diarrheal illnesses. In contrast, Herpesviruses and Poxviruses are double-stranded DNA viruses. The Herpesvirus family includes herpes simplex 1 and 2, varicella-zoster (chicken pox), and Epstein-Barr viruses. The Poxvirus family includes variola (smallpox) and vaccinia viruses.

The ability of protein of the high molecular weight fraction of embryonal extract to inhibit the cytopathic effect of viruses from each of these families of viruses as well as the proliferation of various types of cancer cells suggests that it exerts a generally protective effect on cells which is part of the biologically privileged status of the developing embryo.

3. SUMMARY OF THE INVENTION

In a first embodiment, the present invention relates to a protein comprised in a high molecular weight subfraction of a mammalian embryonal extract and its use as an antiviral agent. This embodiment is based, at least in part, on the discovery that a purified high molecular weight fraction of mammalian embryonal protein exhibited antiviral activity against a spectrum of unrelated viruses, including human immunodeficiency virus type 1, San Angelo virus, simian rotavirus, herpes simplex type I virus, vaccinia virus, and Venezuelan equine encephalitis virus. The antiviral effect may be directed toward a variety of DNA or RNA viruses.

In a second embodiment, the present invention relates to a protein comprised in a high molecular weight subfraction of a mammalian embryonal agent and its use as an antiproliferative (e.g., anticancer) agent. This embodiment is based, at least in part, on the discovery that a purified high molecular weight fraction of mammalian embryonal protein exhibited antiproliferative activity against various types of cancer cells, including lung, breast, and colon cancer cells, leukemic cells, melanoma cells, and non-small cell carcinoma of the lung cells.

In a third embodiment, the present invention relates to purified and isolated peptides having the amino acid sequence Cys Val His A B Arg C, wherein A is selected from the group of amino acids consisting of Ala, Ser and Thr, B is selected from the group of amino acids consisting of Tyr and Phe, and C is selected from a group of amino acids consisting of Ala and Ser.

The present invention also provides for pharmaceutical compositions comprising said proteins and peptides, and for methods of inhibiting virus infection and cell proliferation comprising administering an effective amount of protein(s) or peptide(s) to a subject in need of such treatment. As such, the proteins and peptides of the invention may be useful in the treatment of cancers and infectious diseases.

4. BRIEF DESCRIPTION OF THE FIGURES

FIG. 1. DEAE chromatogram of high-molecular weight material following purification by gel filtration.

Figure 2:
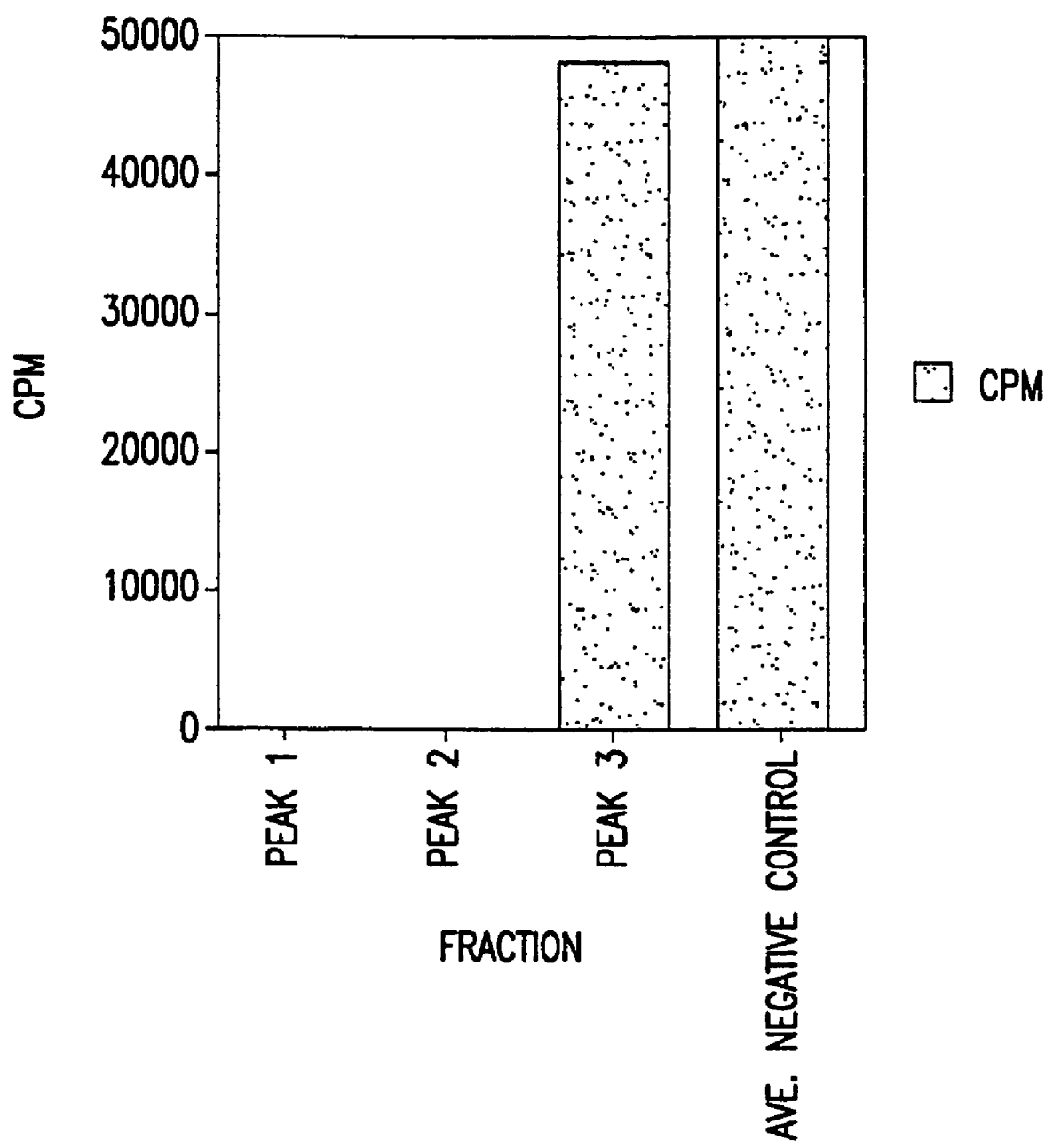

FIG. 2. Antiproliferative effects of material purified by the DEAE batch purification method (which essentially corresponds to peaks 1 and 2 of FIG. 1), as measured by tritiated thymidine uptake.

Figure 3:
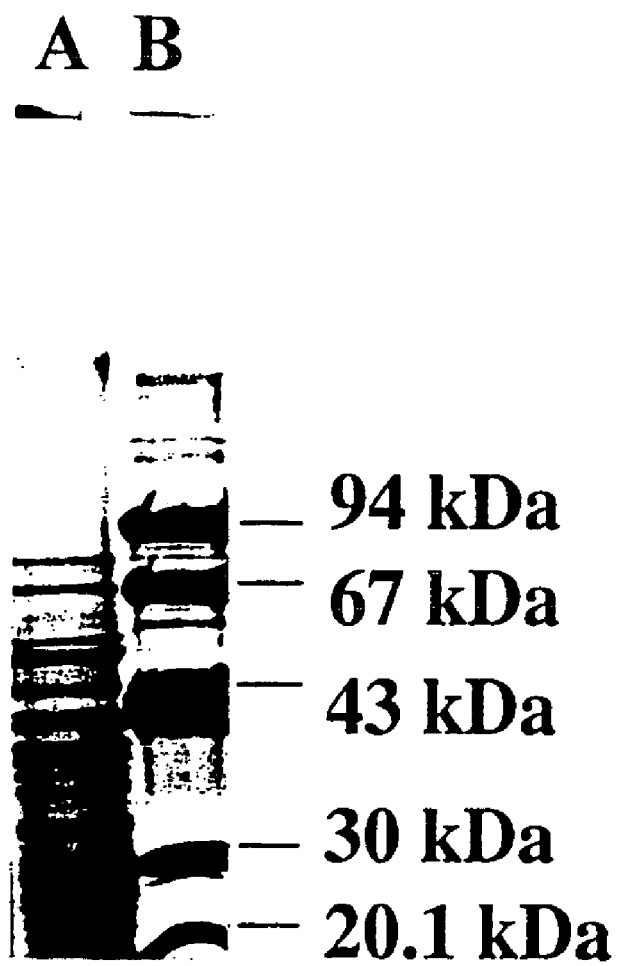

FIG. 3. SDS-Polyacrylamide gel electrophoresis of the high-molecular weight fraction following gel filtration and DEAE purification.

Figure 4:
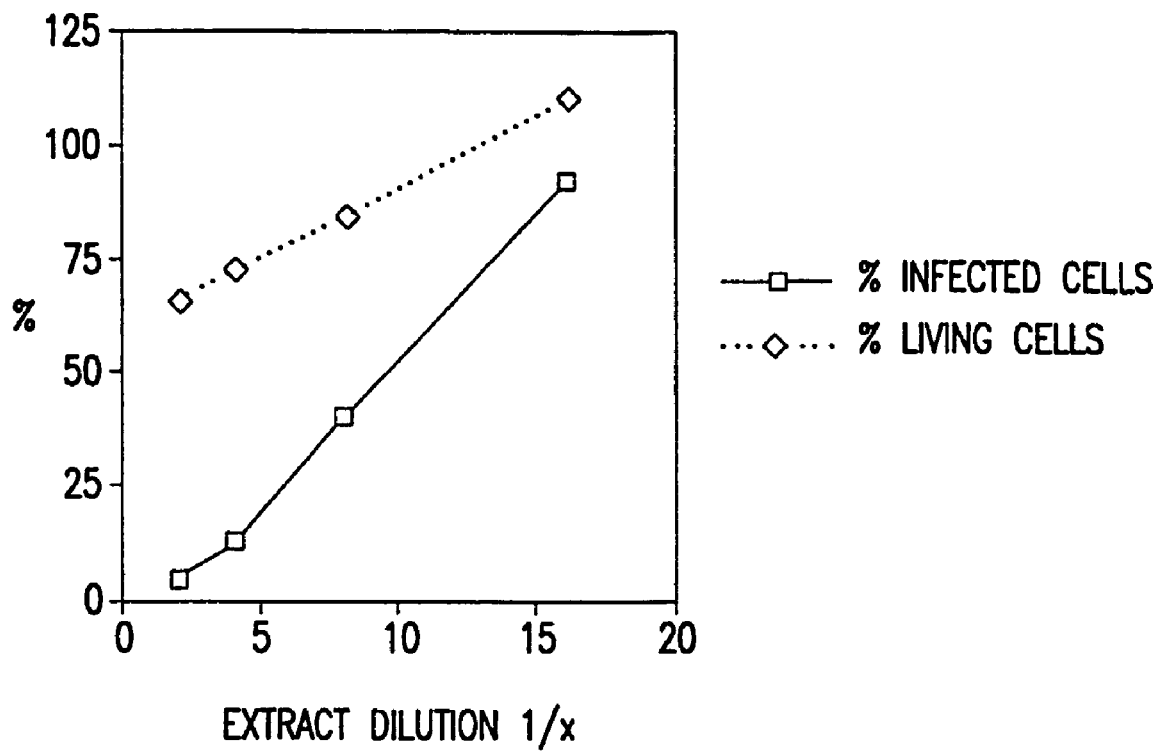

FIG. 4. Effect of high-molecular weight fraction on HIV-1 infection of HeLa P4, showing percent infected cells (square data points) and percent living cells (diamond data points) as a function of the inverse (1/x) of the extract dilution.

Figure 5:
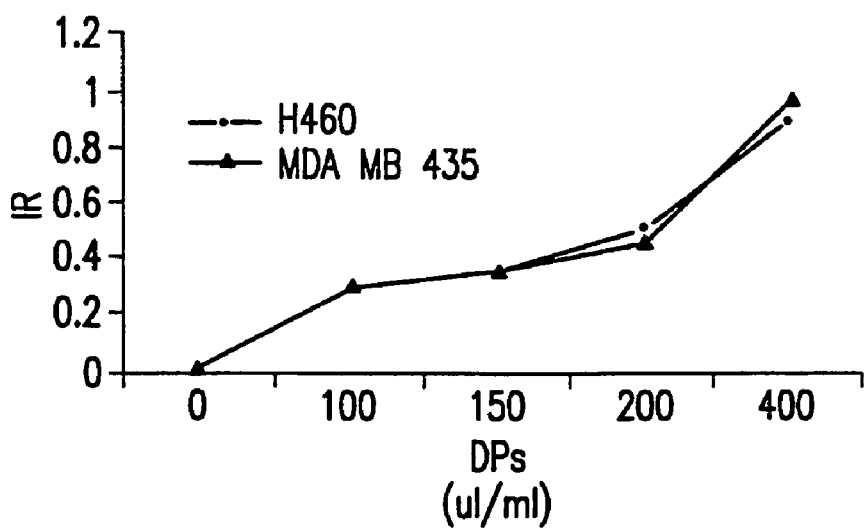

FIG. 5. Effect of high-molecular weight fraction on proliferation of cancer cell lines in vitro, as measured by tritiated thymidine incorporation as a function of the amount of protein present (microliters of extract per milliliter culture medium).

Figure 6A:
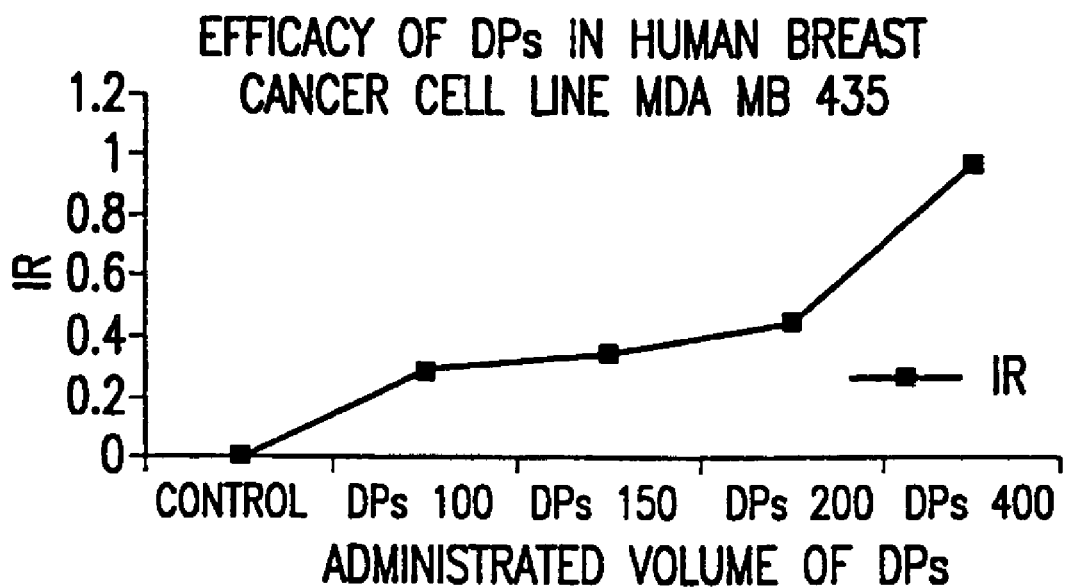
Figure 6B:
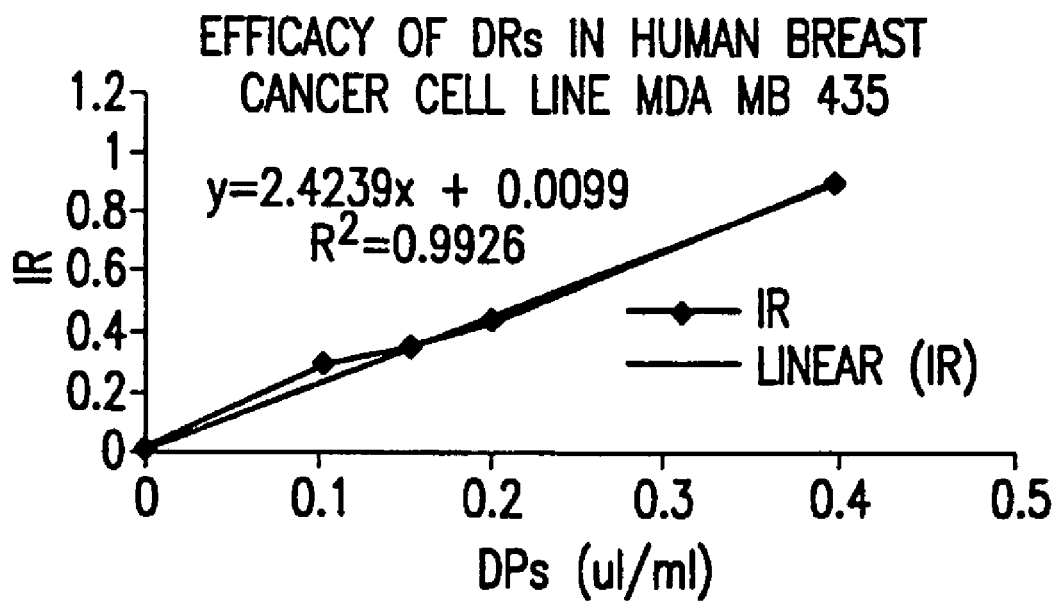

FIG. 6A-B. Effect of high-molecular weight fraction on proliferation of the MDA MB 435 human breast cancer cell line in vitro, as measured by tritiated thymidine incorporation as a function of (FIG. 6A) the volume of extract administered and (FIG. 6B) the amount of protein present (microliters of extract per milliliter culture medium).

Figure 7A:
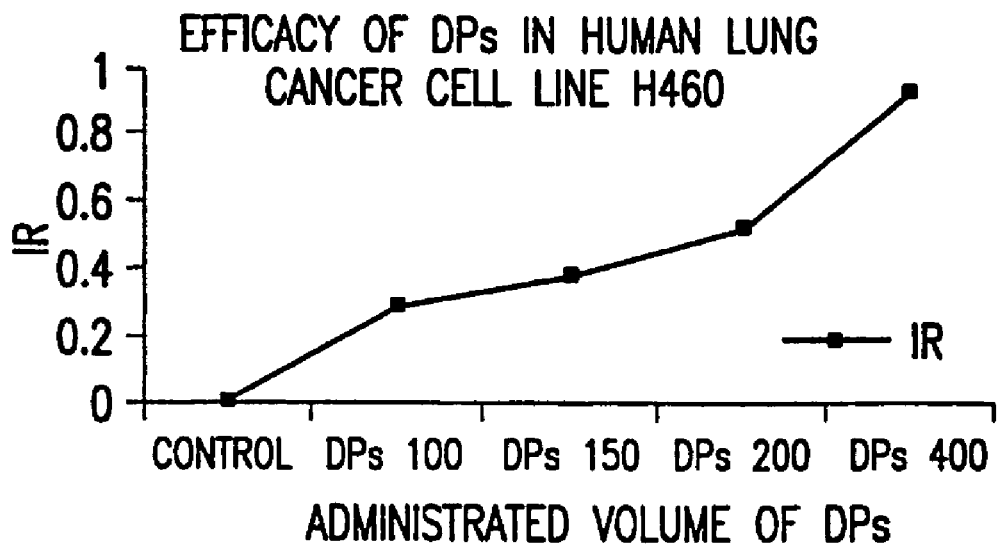
Figure 7B:
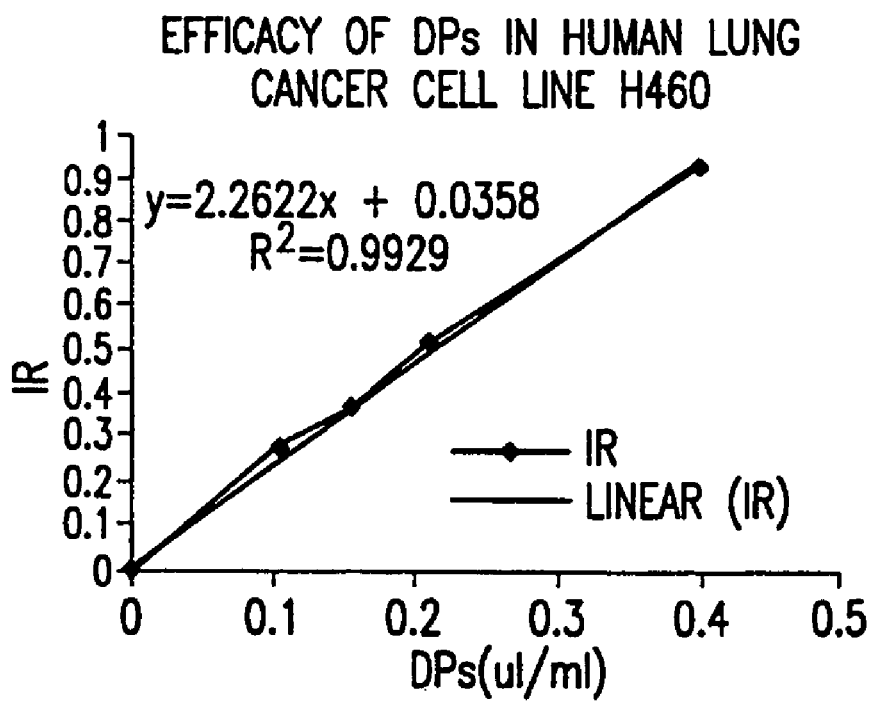

FIG. 7A-B. Effect of high-molecular weight fraction on proliferation of the H460 human lung cancer cell line in vitro, as measured by tritiated thymidine incorporation as a function of (FIG. 7A) the volume of extract administered and (FIG. 7B) the amount of protein present (microliters of extract per milliliter culture medium).

Figure 8:
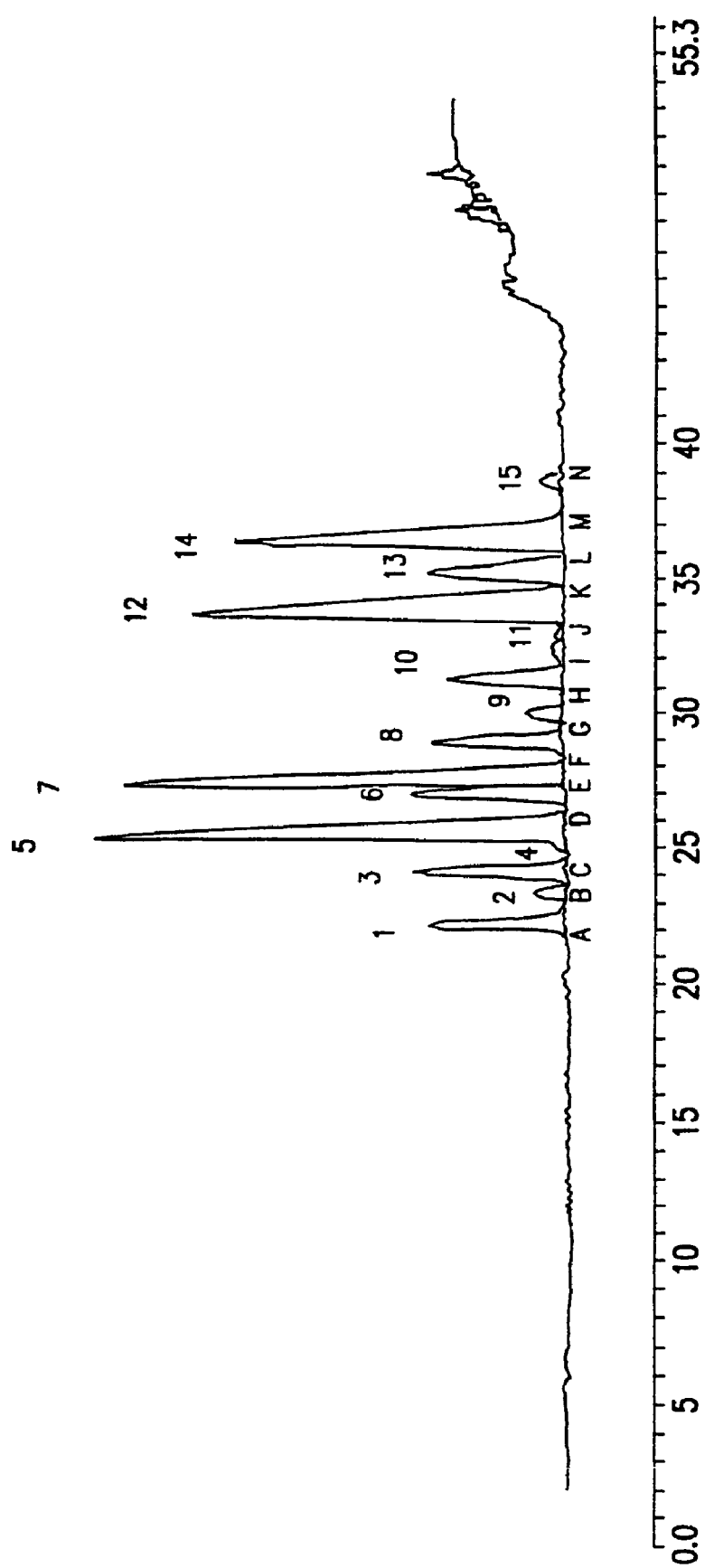

FIG. 8. Combinatorial peptide mixture run on a Phenomenex C5 reverse phase column. Flow rate was 1 ml/min. Buffer A=0.1 percent trifluoroacetic acid in H2; buffer B=0.1 percent trifluoroacetic acid in 99.9 percent acetonitrile. A linear gradient from 0 percent B to 100 percent B in 200 minutes was run. Peaks were monitored at 220 nm.

Figure 9:
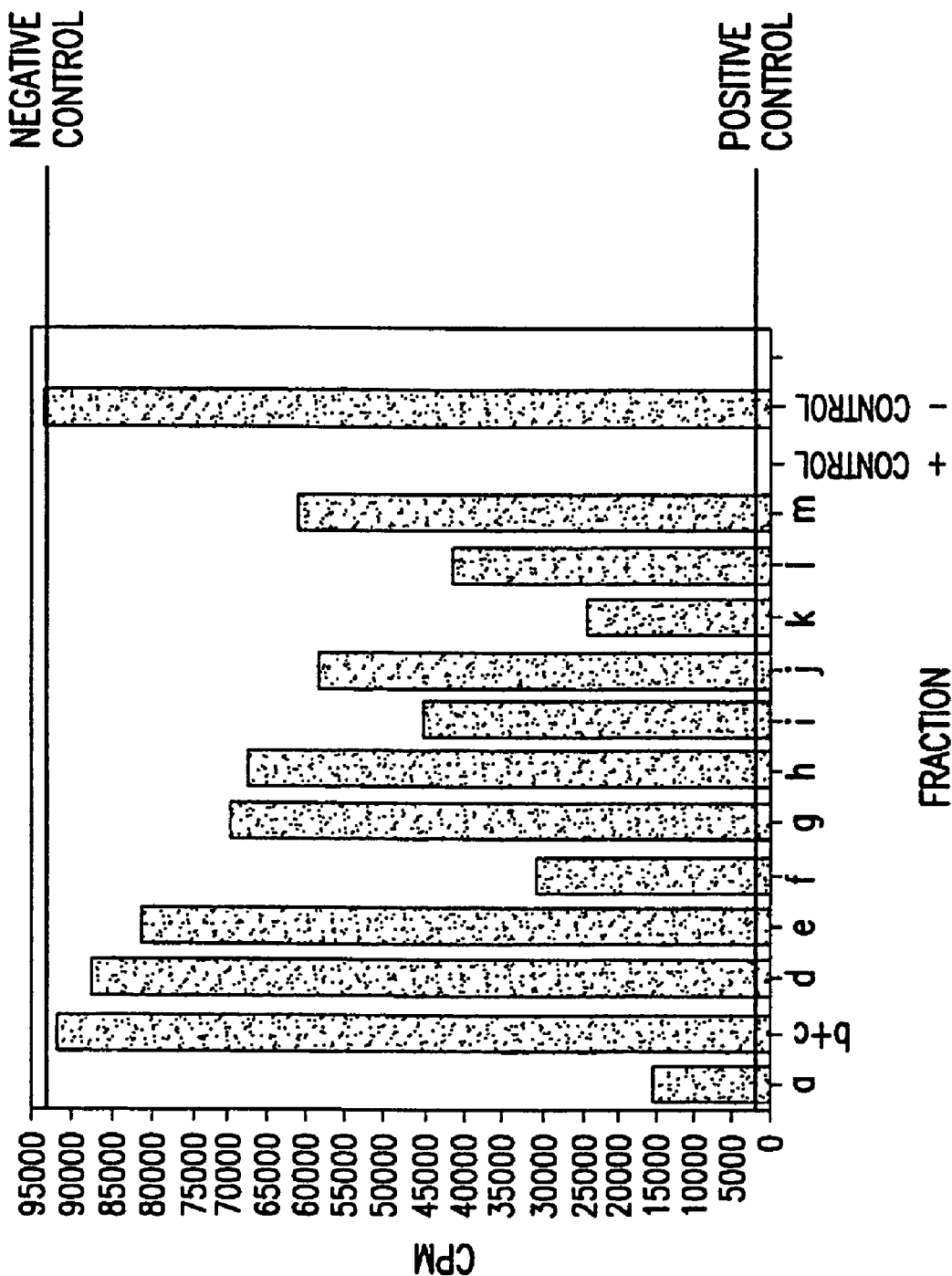

FIG. 9. MCF assay results performed using separated peptides from FIG. 1. The x-axis presents cpm, reflecting radioactivity incorporated by proliferating cells.

Figure 10A:
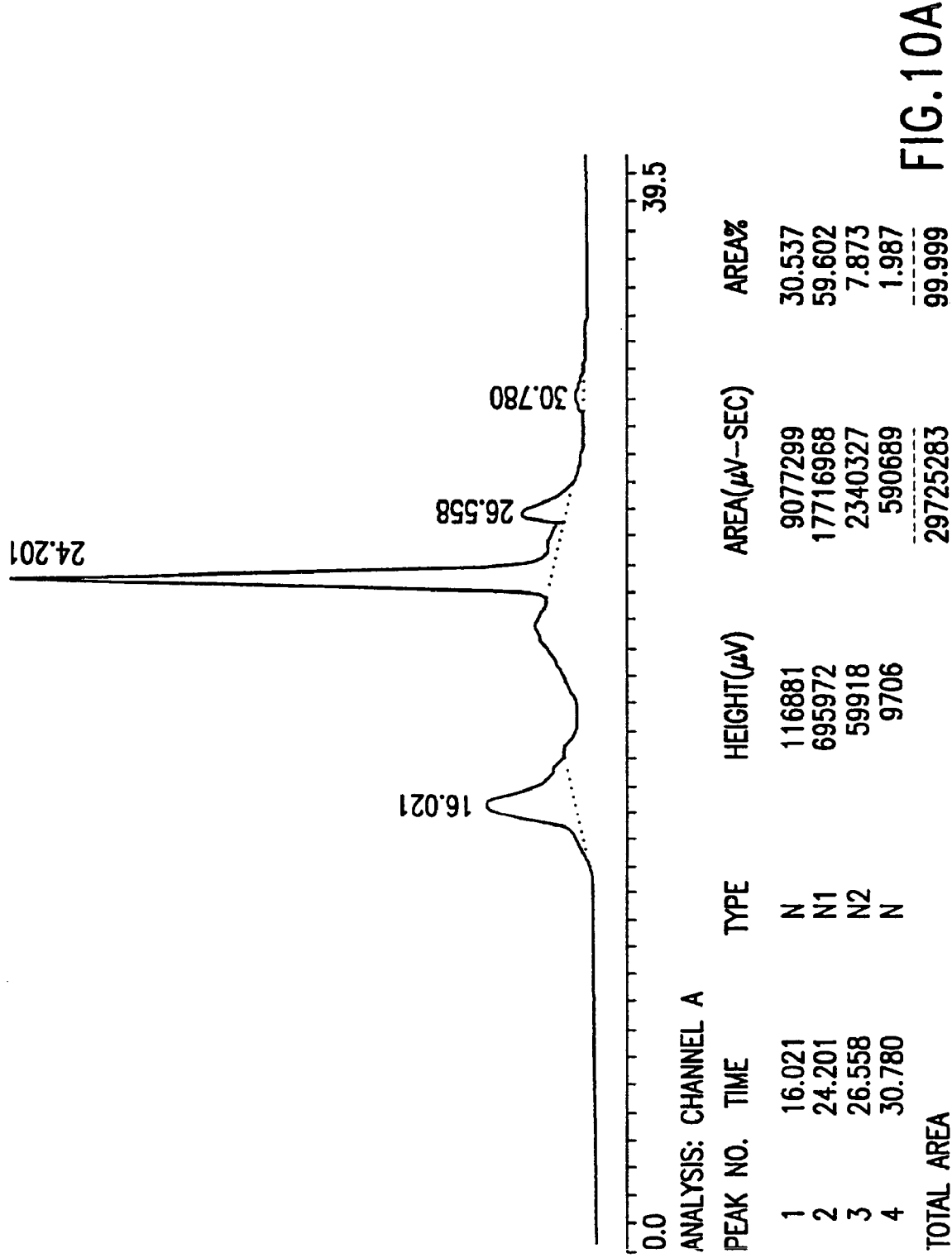

FIG. 10A. HPLC chromatogram where DEAE batch-purified material is further purified on a Progel TSK G2000 gel filtration column (Supelco) eluted with PBS.

Figure 10B:
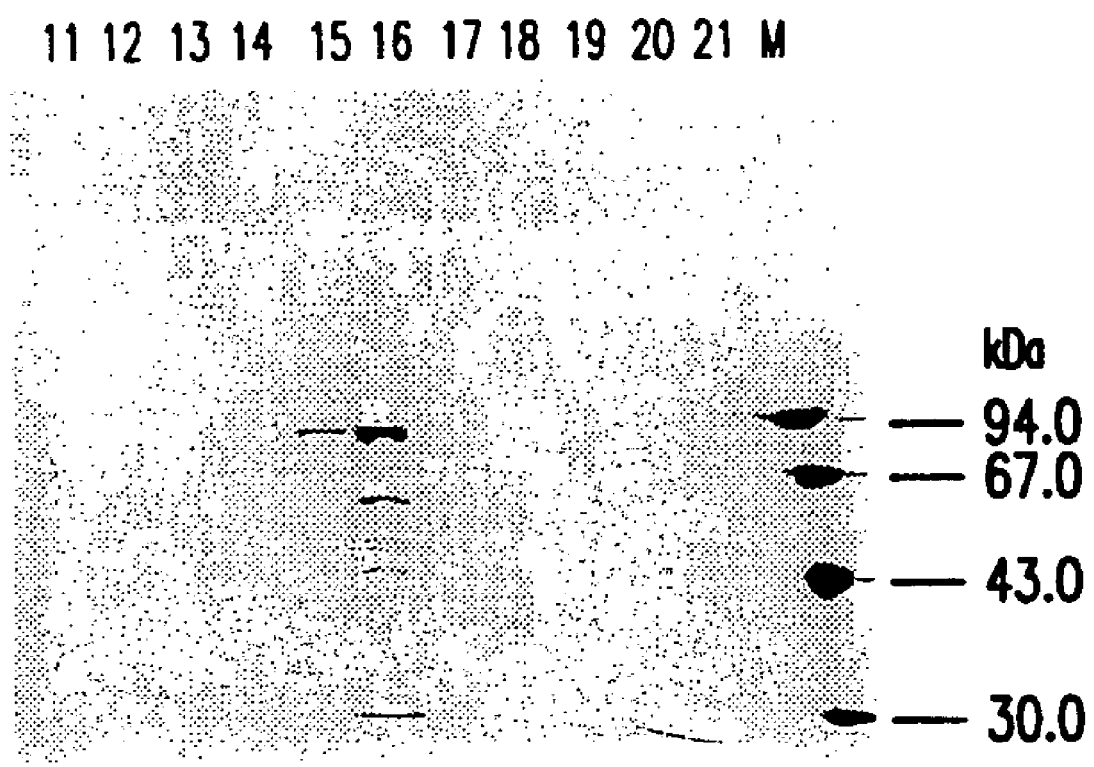

FIG. 10B. SDS polyacrylamide gel electrophoresis of material in active fractions purified according to FIG. 10A.

5. DETAILED DESCRIPTION OF THE INVENTION

For purposes of clarity, and not by way of limitation, the detailed description of the invention is divided into the following subsections.

(a) isolation of high and low molecular weight protein fractions of embryonal extract;

(b) antiviral, antiproliferative proteins from the high molecular weight fractions; and (c) antiproliferative peptides from the low molecular weight fractions.

5.1. Isolation of High and Low Molecular Weight Protein Fractions of Embryonal Extract An embryonal extract may be prepared by solubilizing (homogenizing and/or forming a cell lysate) of a mammalian embryo tissue, including but not limited to a human, pig, cow, horse, sheep or goat embryo tissue, which may constitute the whole embryo or a portion thereof, for example, but not by limitation, the liver or the brain of the embryo. The embryo or tissue may be homogenized and/or used to form a cell lysate by any method known in the art, including, but not limited to, use of a Janke and Kinkel Model T-45 tissue homogenizer, a Dounce tissue homogenizer or sonication. Cell debris may then be removed to produce a supernatant extract, for example by centrifugation for 30 minutes at 18,000 rpm. High molecular weight and low molecular weight fractions may be prepared from the extract as set forth below.

The high molecular weight fraction may be obtained by subjecting the supernatant extract to gel filtration and collecting those fractions which have antiproliferative activity, where such fractions comprise protein having molecular weights greater than 5 kDa, preferably greater than 10 kDa, and more preferably greater than 30 kDa. In specific non-limiting embodiments, the high molecular weight fraction may be prepared by fractionating the embryo extract through a Sephacryl S-100 gel filtration column. If the column is a 750 ml. column, the elution buffer is 50 mM Tris-HCl, pH 7.5, 1 mM dithiothreitol (DTT), and 4-ml. fractions are collected, the higher molecular weight species may typically be obtained from fractions 40-60. A non-limiting example of a protocol which may be used to purify antiviral/antiproliferative protein is set forth below in Sections 6 and 8.

The higher molecular weight fractions from the gel filtration column may be evaluated for their antiproliferative effect on breast cancer cells of the MCF-7 cell line. Fractions exhibiting antiprolerative activity may be utilized for their antiviral effect or further purified.

For example, to achieve higher purification, the higher molecular weight active fractions may be pooled, pH adjusted, for example to pH about 8.5, and applied to an HPLC-DEAE ion exchange column and eluted with a linear gradient of 0-1 M NaCl, and the fractions having an antiproliferative effect on MCF-7 cells collected. An example of such a chromatogram is depicted in FIG. 1. An antiproliferative effect is defined as a decrease in cell proliferation by at least 30 percent.

Still further purification may be achieved by subjecting DEAE-purified material (using either a column or the batch method described below) to cation exchange chromatography on a TSK Gel CM-3SW column. Fractions collected from the column having antiproliferative/antiinfective activity may be identified by measuring inhibition of MCF-7 proliferation.

A preferred method of achieving higher purification of material which has already been purified by gel filtration is a batch method using an ion exchange resin, such as DEAE. Because, as seen in FIG. 1, most antiproliferative activity localizes in early fractions (peaks 1 and 2 in FIG. 1), batch purification achieves efficient purification and may be performed on larger amounts of sample. To perform the batch purification method, higher molecular weight fractions from gel filtration purification (which are 50 mM Tris-HCl) may be pooled, and the pH of the pooled fractions may be adjusted to about pH 8.5 with NaOH. DEAE resin may be pre-equilibrated by soaking in 50 mM Tris-HCl pH 8.5 buffer, in a 2:1 volume of buffer/volume of resin ratio, allowing the resin to settle, pouring off excess buffer, at least twice and until the pH of the supernatant buffer is about 8.5. Then, the DEAE may be collected in a scintered coarse funnel, against vacuum until the resin is just dry, and weighed. The DEAE resin may be combined with the pooled high molecular weight fractions (which are 50 mM Tris-HCl, pH approximately 8.5) in a ratio of 1 gram of resin to 5 ml of pooled fraction material, and mixed for between 1 and 24 hours at 4° C. The resulting resin slurry may then be passed through a coarse scintered funnel, where the collected solution contains purified active sample and the resin may be discarded or regenerated. Preferably, prior to use, the resulting solution may be filter sterilized through, for example, a Millex 0.2μ syringe filter, and stored frozen. Examples of the antiproliferative activity of material purified by the batch purification method are shown in FIG. 2. FIG. 3 depicts the results of SDS-polyacrylamide gel (SDS-PAGE) electrophoresis of high molecular weight fractions purified by gel filtration and DEAE purification methods. Further purification may be achieved by, for example, reverse phase chromatography, preparative gel electrophoresis, or by precipitation or affinity chromatography using antibodies specifically directed toward embryonal proteins. In a specific, non-limiting embodiment of the invention, further purification may be achieved by concentrating material purified by batch DEAE treatment, for example using Centriplus™ (3 kDa cutoff, Amicon, Inc., Beverly Mass.), and applying the concentrate to a Progel TSK G2000 gel filtration column (Supelco), which is then eluted with phosphate buffered saline (PBS) and collected as fractions. An example of an HPLC chromatogram of the material is shown in FIG. 10A. Anitproliferative activity was found in a peak having a retention time of 16.021 minutes, comprising proteins in the 30-50 kDa molecular weight range and corresponding to fractions 15-18 on the chromatogram. SDS polyacrylamide gel electrophoresis of material in these fractions yielded several well-resolved protein bands (FIG. 10B) at molecular weights of approximately 80-90 kDa, 50-60 kDa, and 40-42 kDa.

The low molecular weight fraction may be obtained by fractionating the embryo homogenate through a Sephacryl S-100 gel filtration column. If the column is a 750 ml. column, the elution buffer is 50 mM Tris-HCl, pH 7.5, 1 mM dithiothreitol (DTT), and 4-ml. fractions are collected, the low molecular weight species may typically be obtained from fractions 100-110. A non-limiting example of a protocol which may be used to purify the antiviral protein is set forth below in Section 8. The low molecular weight fractions from the gel filtration column may then be pooled, lyophilized, reconstituted in water and applied to C18 reversed-phase HPLC column. Material may then be eluted from the column using a two-component (A/B) buffer system. Buffer A may be 0.1% trifluoroacetic acid in water; buffer B may be 0.1% trifluoroacetic acid in 99.9% acetonitrile. The column may be developed with a linear gradient of 0-100% buffer B over 1 hour. Fractions may then be collected and tested for biological activity in the MCF-7 assay, and active fractions collected and pooled.

5.2. Antiviral, Antiproliferative Proteins from the High Molecular Weight Fraction The present invention provides for an antiproliferative/antiviral protein, as comprised in the high molecular weight fraction of embryonal extract described above. Accordingly, the present invention provides for therapeutic compositions comprising one or more antiproliferative protein as comprised in a high molecular weight fraction of an embryonal extract prepared by the steps of: a) solubilizing a mammalian embryonal tissue; b) centrifuging the solubilized embryonal tissue to form a supernatant; c) applying the supernatant to a gel filtration column; d) eluting the gel filtration column; e) collecting the eluate as serial fractions; and f) identifying one or more fraction that contains protein having a molecular weight greater than 5 kDa, preferably greater than 10 kDa, and more preferably greater than 30 kDa, and which inhibits the proliferation of a cancer cell. In particular non-limiting embodiments, the present invention provides for antiproliferative/antiviral compositions comprising one or more such protein having a molecular weight of 4-8 kDa, 10-12 kDa, 14-18 kDa, or 30-80 kDa, particularly 40-70 kDa, and more particularly 40-50 kDa or 60-70 kDa. In specific, non-limiting embodiments, the protein may have a molecular weight of approximately 80-90 kDa, 50-60 kDa, 40-42 kDa, 20.1 kDa, 10821 Da, 14832 Da, 14987 Da, 5411 Da or 7477 Da. Said protein may be demonstrated to have antiproliferative and/or antiviral activity, for example, but not by limitation, in an assay using MCF-7 breast cancer cells, where proliferation is inhibited by at least 30 percent and preferably by at least 75 percent, or an assay using simian rotavirus where cytopathic effect is decreased by at least 30 percent and preferably by at least 50 percent. Said compositions may further comprise a suitable pharmaceutical carrier and optionally one or more additional bioactive agent.

In one embodiment of the invention, purified antiviral agent(s) of the high molecular weight fraction may be used to protect cells from viral infection and/or to lessen pathological effects once infection has occurred. The antiviral effects may be produced in vitro or in vivo. The compositions of the invention may thus be used to prevent or to lessen the effects of infection in a subject in need of such treatment.

The agent(s) of the invention may be used as an antiviral agent(s) against infection by DNA and RNA viruses including, but not limited to, members of the Bunyavirus, Togavirus, Reovirus, Herpesvirus and Poxvirus families, as set forth above, as well as, but not limited to, double-stranded DNA viruses such as the Papovaviruses (including Polyoma, SV40, and Papilloma viruses), the Adenoviruses, and the Oridoviruses; single-stranded DNA viruses such as the Parvoviruses (including adeno-associated virus, minute virus of mice, and canine, feline and human parvoviruses); positive-strand RNA viruses such as the Picomaviruses (including polio, common cold, foot and mouth disease, and enteric viruses), and the Coronaviruses (including human common-cold-like diseases and mouse hepatitis virus); negative-strand RNA viruses such as the Rhabdoviruses (including rabies and vesicular stomatitis virus), the Paramyxoviruses (including Newcastle Disease, measles, mumps, respiratory syncytial, and Sendai viruses), the Orthomyxoviruses (such as influenza viruses), and the Arenaviruses (including Lassa virus and lymphocytic choriomeningitis virus); RNA→DNA viruses such as Retroviruses (including human immunodeficiency viruses type 1 and type 2, avian, feline, and murine leukemia viruses and mouse mammary tumor virus), and DNA→RNA viruses such as Hepadnavirus (including Hepatitis B virus).

In a second embodiment of the invention, purified antiproliferative agent(s) of the high molecular weight fraction may be used to protect cells from malignant transformation or decrease proliferation of malignant cells. The antiproliferative effects may be produced in vitro or in vivo. In particular embodiments, the antiproliferative agent(s) of the high molecular weight fraction may be used to prevent and/or inhibit the proliferation of, and to treat, cancers involving the breast, lung, prostate, bone, liver, lymphocytes, squamous epithelium, melanocytes, colon, stomach, pancreas, esophagus, skin, testicle and nervous system. The agent(s) of the high molecular weight fraction have been demonstrated to inhibit in vitro the proliferation of human breast and lung cancer cells, lymphoblastic and promyelocytic leukemia cells, non-small cell carcinoma of the lung cells (line NCIH226), colon cancer cells (lines COLO205, SW620), central nervous system cells (SF-539) and melanoma cells (lines SK-MEL 28 and SK-MEL 5). The compositions of the invention may thus be used to prevent or to inhibit the growth or spread of malignant cells in a subject in need of such treatment.

5.3. Antiproliferative Peptides from the Low Molecular Weight Fraction

The present invention relates to compositions comprising one or more of the following purified and isolated heptapeptides, and for peptides and proteins comprising the following peptides.

Cys Val His Ala Tyr Arg Ser (SEQ ID NO:1);
Cys Val His Ala Tyr Arg Ala (SEQ ID NO:2);
Cys Val His Ala Phe Arg Ser (SEQ ID NO:3);
Cys Val His Ala Phe Arg Ala (SEQ ID NO:4);
Cys Val His Ser Tyr Arg Ser (SEQ ID NO:5);
Cys Val His Ser Tyr Arg Ala (SEQ ID NO:6);
Cys Val His Ser Phe Arg Ser (SEQ ID NO:7);
Cys Val His Ser Phe Arg Ala (SEQ ID NO:8);
Cys Val His Thr Tyr Arg Ser (SEQ ID NO:9);
Cys Val His Thr Tyr Arg Ala (SEQ ID NO:10);
Cys Val His Thr Phe Arg Ser (SEQ ID NO:11); and
Cys Val His Thr Phe Arg Ala (SEQ ID NO:12).

In preferred embodiments the peptides and proteins of the invention comprise peptides having sequences as set forth in SEQ ID NOS 2, 3, and 8.

Such peptides may also be modified by conjugation to another compound, where said compound is selected from the group including, but not limited to, other proteins (e.g. immunoglobulin molecules or fragments thereof), carbohydrate residues, pharmaceutical agents, polyethylene glycol, etc., or may be incorporated into a larger peptide or protein, e.g., a fusion protein.

The present invention provides for isolated nucleic acids encoding the peptides of the invention. Such peptides may be comprised in a suitable vector for cloning and/or expression.

The present invention also provides for peptides as set forth above prepared by producing a combinatorial mixture of each of the possible peptides and subjecting the mixture to reverse phase chromatography as set forth below and as depicted in FIG. 8. Fractions that migrate at positions set forth in FIG. 8 as peaks A, F and K are particularly preferred for use as antiproliferative agents.

The peptides of the invention may be prepared from natural sources, chemically synthesized, or produced by recombinant DNA methods. The present invention also provides for the introduction, into a subject, of a nucleic acid encoding one or more of the foregoing peptides, operatively linked to a promoter element, such that the encoded peptide or peptides are expressed. The subject may be a microorganism, such as a bacterium or yeast, a eukaryotic cell, such as a mammalian, insect, or plant cell, or may be a multicellular organism, such as a mammal or bird.

The antiproliferative peptides of the invention may be used in methods of inhibiting cell proliferation, and particularly inhibiting malignant cell proliferation. They may be administered, in an effective dose and in a suitable pharmaceutical carrier, to a subject in need of such treatment. Administration methods include but are not limited to, topical, intravenous, oral, intrapulmonary, intrathecal, subcutaneous, intradermal, intramuscular, intraperitoneal, as well as local injection into a tissue or tumor. Proliferative conditions which may benefit from the administration of peptides of the invention include, but are not limited to, cancers, including but not limited to breast cancer, prostate cancer, colon cancer, lung cancer, cancers of the stomach, skin, brain, muscle, pancreas, liver, and bladder; and nonmalignant proliferative conditions such as neoplasms such as breast adenomas and hyperproliferation of tissues as occurs in rheumatoid arthritis and keloid formation.

The peptides of the invention may be used as antiinfective agents. As such, they may be used to inhibit the proliferation of viruses, and particularly viruses such as influenza virus, vaccinia virus and human immunodeficiency virus.

6. EXAMPLE

ANTIVIRAL EFFECTS OF EMBRYONAL PROTEINS

6.1. Materials and Methods

6.1.1. Preparation of Purified Embryonal Protein(s)

Five grams of liver harvested from porcine embryos was homogenized for 1 minute at 4° C. in extraction buffer (50 mM Tris, pH 7.5; 1 mM PMSF; 1 mM benzamidine, 10 μg/ml pepstatin, and 1 mM DTT; where the extraction buffer volume/liver weight ratio was 3:1) using a Janke and Kinkel Model T-45 tissue homogenizer. The homogenate was then centrifuged at 18,000 rpm for 30 minutes in a Beckman J2-21 centrifuge. The pellet was discarded and the supernatant was applied to a 750 ml Sephacryl S-100 column (Pharmacia) and eluted with 50 mM Tris-HCl, pH 7.5, 1 mM DTT, at 4° C. Fractions containing about 4 ml were collected, sterilized by filtration through 0.2 μm filters (Millex) and assayed using the MCF-7 assay described above. Active material was pooled and stored at −80° C. Active fractions containing high molecular weight species (approx. fractions 40-60) were used for the experiments below.

6.1.2. Viruses

The following viruses were used: San Angelo (SAV, a member of the Bunyaviridae family), original strain, obtained from the American Type Culture Collection (ATCC, Rockville, Md.); Venezuelan equine encephalitis (VEE, a member of the Togaviridae family), strain Trinidad (TC-attenuated), obtained from the ATCC; simian rotavirus (SRV, a member of the Reoviridae family), strain SA11, obtained from Dr. Mary Estes, Baylor College of Medicine, Houston, Tex.; type 1 herpes (HSV-1, a member of the Herpesviridae family), strain McKrae, provided by Dr. A. B. Nesburne of the Estelle Doheny Eye Foundation, Los Angeles, Calif.; and vaccinia virus (VV, a member of the Poxviridae family), strain Lederle chorioallantoic, obtained from the ATCC. A pool of each was prepared in the appropriate cell cultures, ampuled, frozen at −80° C., and titrated in vitro prior to use in this study.

6.1.3. Cells and Media

The SAV test was run in African green monkey kidney (Vero) cells using as growth medium minimum essential medium (MEM) with 0.1% $NaHCO_3$ and 5% fetal bovine serum (FBS) and MEM +2% FBS, 0.1% $NaHCO_3$ and 50 μg/ml gentamicin for the antiviral test. Testing versus VEE was done in MA104 cells with the same medium as described above for cell growth, and MEM +0.18% $NaHCO_3$ and 50 μg/ml gentamicin without FBS for the antiviral test. The SRV test was also run in MA104 cells with the same medium as described above for VEE with the addition of 2 μg/ml trypsin. The HSV-1 tests were performed using the human embryonic lung cell line MRC-5 with growth medium being basal medium Eagle (BME), 10% FBS, 0.035% $NaHCO_3$, and antiviral test medium being MEM with 2% FBS, 0.18% $NaHCO_3$ and 50 μg/ml gentamicin. VV tests were run in African green monkey cells (CV-1) with growth medium being MEM, 10% FBS, and 0.05% $NaHCO_3$, and test medium being MEM +2% FBS and 50 μg/ml gentamicin.

6.1.4. Positive Controls

The following compounds were used as positive controls run with the appropriate tests: acyclovir (Glaxo-WellcomE, Research Triangle Park, N.C.), cidofovir (Gilead Sciences, Foster City, Calif.), and ribavirin (ICN Pharmaceuticals, Costa Mesa, Calif.). Each was dissolved in cell culture medium for use in this study at the concentrations indicated below.

6.1.5. Measurement of Viral Cytopathic Effect

Antiviral effect was measured as a reduction in viral induced cytopathic effect (CPE). Seven one-half $\log_{10}$ dilutions of purified embryonal protein, beginning at a dilution of 1:5, and the appropriate known positive control drug at pre-determined concentrations in a volume of 0.1 ml were placed on the appropriate 24 hour monolayer of cells in 96-well flat-bottomed microplates. Approximately 5 minutes later, the test virus in a volume of 0.1 ml was added to the cells, using 4 microplate cups/dilution of protein. Toxicity control wells (2 cups/drug concentration) received 0.1 ml of test medium; virus control wells (8 wells) were exposed to test medium and virus, and normal control wells (4 wells) received test medium only. Each microplate contained the tests for both protein and the positive control drug. The microplates were sealed with plastic wrap and incubated in a humidified incubator at 37° C. until CPE, determined by microscopic examination of the plate, had reached near-maximal (3-4+) levels. The microplates were then examined by a technician trained for such cell examination, and viral CPE scores of 0 (normal) to 4 (maximum CPE) assigned to each cup containing virus. Toxicity was also ascertained microscopically with the degree of toxicity, as evidenced by aberrant cell appearance, assigned scores ranging by 20% increments. The CPE inhibition data were plotted against protein dilution, and a line of best fit used to determine a 50% effective (viral CPE-inhibitory) dose (EC50). The toxicity data were similarly plotted to determine a 50% cytotoxic (cell-inhibitory) concentration (CC50). A selectivity index (SI) was determined as the CC50÷EC50. Positive control compounds were, for SAV, VEE, and SRV, ribavirin; for HSV-1, acyclovir; and for VV, cidofovir (HPMPC). This method has been previously described in Sidwell and Huffman, 1971, Appl. Microbiol. 22:797-801; Sidwell, et al. 1972, Science 177:705-706; Barnard, et al., 1993, Chemotherapy 39:203-211; Huffman, et al., 1997, Antiviral Chem. and Chemother. 8:75-83: and Barnard, et al., 1997, Anti. Chem. and Chemother. 8:223-233.

6.1.6. Neutral Red Assay

The above CPE inhibition tests were validated by adding neutral red dye to the cells; the cells not damaged by virus take up a greater amount of dye, which is read on a computerized microplate autoreader. This method has been fully described in Barnard et al., 1993, Chemotherapy 39:203-211; Huffman et al., 1997, Antiviral Chem. And Chemother 8:75-83; Barnard et al., Anti. Chem. And Chemother 8:223-233. EC50, CC50, and SI were again determined by the dye uptake method.

6.2. Results and Discussion

The results of the tests with SAV, SRV, HSV-1 and VV are shown in Tables I-V below.

Against SAV (Table I), the embryonal protein was moderately inhibitory, with an EC50 of 7.7% (neutral red) and 12.5% (visual CPE method). The compound caused only slight cytotoxicity at the highest dose tested, 20%, so a CC50 could not be determined. Ribavirin exerted the positive activity seen previously; we are not aware of any published reports of the activity of ribavirin versus SAV, although the related Bunyaviridae viruses Hantaan (Kirsi et al., 1983, Antimicrob. Ag. Chemother. 24:353-361), LaCrosse (Cassidy and Patterson, 1989, Antimicrob. Ag. Chemother. 33:2009-2013), Punta Toro (Sidwell et al., 1988, Antimicrob. Ag. Chemother. 32:331-336; Huffman et al., 1989, Nucleotides and Nucleosides 8:1159-1160), and Rift Valley Fever (Stephen et al., 1980, in "Ribavirin: A Broad-Spectrum Antiviral Agent", (Smith and Kirkpatrick, eds.) Academic Press, NY, pp. 169-183) have been reported to be sensitive to this compound.

SRV (Table II) was also moderately inhibited by embryonal protein, the EC50 values being as low as 1.6%. A CC50 value of 11% was seen using this compound in MA-104 cells using visual examination of the cells, but by neutral red dye uptake, any cytotoxic effect seen was minimal. Ribavirin was weakly effective against this virus; this activity was in the range reported previously (Smee et al., 1981, Proc. Intl. Conf. On Neonatal Diarrhea Vet. inf. Dis. Org., Saksatoon, pp. 123-136).

Similar antiviral activity was seen against HSV-1 (Table III), the EC50 values being 10-12%, with no detectable CC50. Acyclovir, used as the positive control drug, exerted the activity expected as has been reported by others (Elion, 1982, Am. J. Med. 73:7-13).

Against VV (Table IV), no activity was discernible by visual cell examination, but by the neutral red dye uptake test, an EC50 of 8.4% was seen. In the CV-1 cells, a visual CC50 of 11% was observed, but this could not be confirmed by neutral red uptake. This difference in cytotoxicity results is not uncommon, since visual examination may detect minor cell changes denoting effect of test drug, but the cells remain sufficiently viable to take up the dye in a normal manner. Cidofovir (HPMPC) was active against VV; we are unaware of reports of the in vitro VV-inhibitory effects of this compound, but strong efficacy has been reported against the infection in mice (Neyts and DeClerq, 1993, J. Med. Virol. 41:242-246).

The activity of the embryonal protein against VEE (Table V) was similar to its activity against the other viruses, although in one set of experiments some cells were seen to be washed from the plate during the rinsing steps of the neutral red assay.

Each of the viruses used in these experiments have significant public health importance, or are related to viruses that do. Bunyaviruses cause a number of diseases, including Rift Valley fever, Sandfly fever, and Crimean-Congo hemorrhagic fever. The Togaviruses of importance include particularly VEE, but also include a number of other encephalitis viruses such as eastern and western equine encephalitis, and Chikungunya. The SRV is closely related to human rotavirus, a major cause of diarrhea in developing nations around the world. Many of the Herpesviruses, including HSV-1, HSV-2, cytomegalovirus, varicella and Epstein-Barr viruses, are important pathogens. VV represents the poxviruses which include smallpox virus which could become a major biological warfare threat.

These data indicate that agent(s) present in the high molecular weight fraction of embryonal extract has potentially a broad-spectrum antiviral effect. The lack of cytotoxicity enhances the clinical potential of this compound. The protein purified from embryonal extract was found to have inhibitory affects against a spectrum of unrelated viruses, included San Angelo, simian rotavirus, type 1 herpes, and vaccinia.

TABLE I

Test Virus = San Angelo Virus

| | |
|---|---|
| EXPT. # | EV/SAC1 - visual |
| COMPOUND # | Embryonal Protein |
| CC50: | >20% |
| EC50: | 12.5% |
| SI: | >1.6 |
| COMMENT: | Slight activity. |
| EXPT. # | EV/SAC1 - neutral red assay |
| COMPOUND # | Embryonal Protein |
| CC50: | >20% |
| EC50: | 7.7% |
| SI: | >2.6 |
| COMMENT: | Moderate activity. |
| EXPT. # | EV/SAC2 - visual |
| COMPOUND # | Ribavirin |
| CC50: | 560 µg/ml |
| EC50: | 30 µg/ml |
| SI: | 19 |
| COMMENT: | Very good activity. |
| EXPT. # | EV/SAC2 - neutral red assay |
| COMPOUND # | Ribavirin |
| CC50: | 530 µg/ml |
| EC50: | 30 µg/ml |
| SI: | 18 |
| COMMENT: | Very good activity. |

TABLE II

Test Virus = Simian Rotavirus

| | |
|---|---|
| EXPT. # | EV/RtC1 - visual |
| COMPOUND # | Embryonal Protein |
| CC50: | 11% |
| EC50: | 1.6% |
| SI: | 6.9 |
| COMMENT: | Moderate activity. |
| EXPT. # | EV/RtC1 - neutral red assay |
| COMPOUND # | Embryonal Protein |
| CC50: | >20% |
| EC50: | 3% |
| SI: | >6.7 |
| COMMENT: | Moderate activity. |
| EXPT. # | EV/RtC2 - visual |
| COMPOUND # | Ribavirin |
| CC50: | >100 µg/ml |
| EC50: | 18 µg/ml |
| SI: | >5.6 |
| COMMENT: | Moderate activity. |
| EXPT. # | EV/RtC2 - neutral red assay |
| COMPOUND # | Ribavirin |
| CC50: | >100 µg/ml |
| EC50: | 56 µg/ml |
| SI: | >1.6 |
| COMMENT: | Slight activity. |

TABLE III

Test Virus = Herpes Simplex Type I

| | |
|---|---|
| EXPT. # | EV/H1C1 - visual |
| COMPOUND # | Embryonal Protein |
| CC50: | >20% |
| EC50: | 12% |
| SI: | >1.7 |
| COMMENT: | Slight activity. |
| EXPT. # | EV/H1C1 - neutral red assay |
| COMPOUND # | Embryonal Protein |
| CC50: | >20% |
| EC50: | 10% |
| SI: | >2 |
| COMMENT: | Slight activity. |
| EXPT. # | EV/H1C2 - visual |
| COMPOUND # | Acyclovir |

TABLE III-continued

Test Virus = Herpes Simplex Type I

| | |
|---|---|
| CC50: | >100 µg/ml |
| EC50: | 0.6 µg/ml |
| SI: | >167 |
| COMMENT: | Excellent activity. |
| EXPT. # | EV/H1C2 - neutral red assay |
| COMPOUND # | Acyclovir |
| CC50: | >100 µg/ml |
| EC50: | 0.4 µg/ml |
| SI: | >250 |
| COMMENT: | Excellent activity. |

TABLE IV

Test Virus = Vaccinia Virus

| | |
|---|---|
| EXPT. # | EV/VC1 - visual |
| COMPOUND # | Embryonal Protein |
| CC50: | 11% |
| EC50: | >20% |
| SI: | <0.6 |
| COMMENT: | Essentially no activity. |
| EXPT. # | EV/VC1 - neutral red assay |
| COMPOUND # | Embryonal Protein |
| CC50: | >20% |
| EC50: | 8.4% |
| SI: | >2.4 |
| COMMENT: | Slight activity. |
| EXPT. # | EV/VC2 - visual |
| COMPOUND # | HPMPC |
| CC50: | >100 µg/ml |
| EC50: | 5.4 µg/ml |
| SI: | >18 |
| COMMENT: | Very good activity. |
| EXPT. # | EV/VC2 - neutral red assay |
| COMPOUND # | HPMPC |
| CC50: | >100 µg/ml |
| EC50: | 1.7 µg/ml |
| SI: | >59 |
| COMMENT: | Excellent activity. |

TABLE V

Test Virus = Venezuelan Equine Encephalitis

| | |
|---|---|
| EXPT. # | EV/VEC3 - visual |
| COMPOUND # | Embryonal Protein |
| CC50: | >20% |
| EC50: | 13% |
| SI: | >1.5 |
| COMMENT: | Slight activity. |
| EXPT. # | EV/VEC3 - neutral red assay |
| COMPOUND # | Embryonal Protein |
| CC50: | >20% |
| EC50: | 17% |
| SI: | >1.2 |
| COMMENT: | Slight activity. Some cells were lost from the plate during the rinsing process; thus, the neutral red data is questionable. |
| EXPT. # | EV/VEC4 - visual |
| COMPOUND # | Ribavirin |
| CC50: | >100 µg/ml |
| EC50: | 7.6 µg/ml |
| SI: | >13 |
| COMMENT: | Very good activity. |
| EXPT. # | EV/VEC4 - neutral red assay |
| COMPOUND # | Ribavirin |
| CC50: | >100 µg/ml |
| EC50: | >100 µg/ml |
| SI: | ? |
| COMMENT: | No activity seen. Some cells were lost from the plate in the rinsing process; thus, the neutral red data is questionable in this experiment. |

7. EXAMPLE

ANTIVIRAL EFFECTS AGAINST HUMAN IMMUNODEFICIENCY VIRUS TYPE 1

The ability of agent(s) present in the high molecular weight fraction of embryonal extract to inhibit infection by human immunodeficiency virus type-1 (HIV-1) was tested using CD4+ HeLa P4 indicator cells containing the LacZ reporter gene under control of the viral long terminal repeat (LTR). Viral entry up-regulates the expression of the reporter construct, allowing quantification of infection by measuring LacZ activity. High molecular weight embryonal extract was prepared by gel filtration as set forth above in Section 6. Indicator cells were introduced into microplate wells at a concentration of $10^4$ cells per well and cultured overnight. The media was then exchanged against 100 µl of high molecular weight embryonal fraction in dilutions with medium as indicated on FIG. 4, and the cells were infected with 100 µl of virus (HIV-1, NDK, 2 µg p24/ml) and incubated for 24 hours. The supernatant was then taken off, and the cells were lysed with 50 µl /well of PBS/1% NP40. Then 50 µl per well of indicator substrate (CPRG) was added, and the OD at 575 nm was measured.

To determine the effect of extract on cell viability, the cultures were subjected to an MTT assay as follows. Cells were treated and infected as described in the preceding paragraph. After 24 hours, the cells were supplemented with medium containing MTT and incubated for a further 3 hours. The supernatant was then taken off, and the cells were lysed in acidified isopropanol and the OD measured at 575 nm.

FIG. 4 shows the results of the infection and toxicity assays, which indicate that viral infection was effectively inhibited at concentrations which were not substantially toxic to the cells.

When infectivity assays for reverse transcriptase production were performed using feline immunodeficiency virus (FIV, strain FIVWO) and feline peripheral blood lymphocytes, no inhibition was observed.

8. EXAMPLE

PROTEINS OF THE HIGH MOLECULAR WEIGHT FRACTION INHIBIT THE PROLIFERATION OF CANCER CELLS

The ability of agent(s) present in the high molecular weight fraction of embryonal extract to inhibit proliferation of cancer cells was tested in the human lung cancer cell line H460 and the human breast cancer cell line MDA MB-435. High molecular weight embryonal extract was prepared by gel filtration as set forth above in Section 6 and further purified using DEAE sepharose. Human lung cancer cell line H460 and human breast cancer cell line MDA MB-435 were obtained from the National Cancer Institute in Frederick, Md. The assays were performed in monolayer cell culture, wherein in vitro IC50 concentrations were determined using a tritiated thymidine incorporation assay. A total of 15 wells for each cell line were tested.

In particular, the tritiated thymidine assays were performed as follows. $1\times10^4$ cells were plated in 1 ml of RPMI 1640 medium containing 10% fetal bovine serum (FBS) in 24-well plates. The cultures were incubated for 24 hours at 37° C., 5% carbon dioxide. High molecular weight fraction was added to each corresponding well and incubation was allowed to proceed for an additional 72 hours. The cells were then exposed to tritiated thymidine at a concentration of 1 µCi/ml (ICN, Cat. # 2403905 and incubated at 37° C. for four hours. The cells were then washed twice with cold PBS to remove non-incorporated thymidine. The cells were treated twice with 10% trichloroacetic acid (Fisher, Lot #94276913), 1 ml per well. The cells were then disrupted by treatment with 10% sodium lauryl sulfate (Sigma, Cat. #L-3771) at 500 µl per well. Cells from each well were transferred to a scintillation vial and counted in a Beckman Model LS-133 scintillation counter. The results are shown in Tables VI and VII and FIGS. 5-7. The data showed statistically significant inhibition of cell growth, compared to control, when 200 or 400 µl/ml medium of high molecular weight embryonal extract were used for H460 lung cancer cells (P=0.03, P=0.001), and for all dilutions (100-400 µl extract/ml medium) for MDA MB 435 cells.

TABLE VI

Inhibition of human cancer cell line H460 after treatment with extract

| Dose extract (µl/ml) | Thymidine Incorporation (mean cpm) | Inhibitory response (IR) | p-value* |
|---|---|---|---|
| 0 | 110207 ± 4706 | 0 | |
| 100 | 78208 ± 39520 | 29% | 0.289 |
| 150 | 68630 ± 34418 | 38% | 0.206 |
| 200 | 53499 ± 15597 | 51% | 0.03 |
| 400 | 8863 ± 88 | 92% | 0.001 |

*Student's t-test

TABLE VII

Inhibition of human breast cancer line MDA MB435 after treatment with extract

| Dose extract (µl/ml) | Thymidine Incorporation (mean cpm) | Inhibitory response (IR) | p-value* |
|---|---|---|---|
| 0 | 158195 ± 18458 | 0 | |
| 100 | 111251 ± 7413 | 30% | 0.034 |
| 150 | 100715 ± 10505 | 36% | 0.019 |
| 200 | 85256 ± 6676 | 46% | 0.022 |
| 400 | 2082 ± 463 | 99% | 0.005 |

*Student's t-test

Inhibition is depicted in FIG. 5, FIGS. 6A and 6B, and FIGS. 7A and 7B for pooled results for both lines and for the MDA MB 435 and H460 lines, respectively, in particular. IC50s were calculated by graphing the dose response curves for the high molecular weight extract for H460 and MDA MB 435 using Microsoft Excel. A trend line was established and inhibitory concentrations were extrapolated by identifying the convergence of the 0.5 IR to the extract volume along the dost response curve. The 50 percent inhibitory concentration for H460 was determined to be 205 µl/ml. The 50 percent inhibitory concentration for the MDA MB 435 was determined to be 202 µl/ml. For MDA-MB 435 human breast cancer cells and H460 lung cancer cells, inhibitory activity obtained was 99% and 92%, respectively.

9. EXAMPLE

CHARACTERIZATION OF LOW-MOLECULAR WEIGHT ANTIPROLIFERATIVE PEPTIDES

Livers from porcine embryos were homogenized in a buffer containing an anti-proteolytic cocktail and fractionated by passage through a large (750 ml) Sephacryl S-100 gel filtration column. Four ml fractions were collected and assayed for activity by adding them to cultured MCF-7 cells followed, in 4 days, by a determination of the uptake of radiolabeled thymidine by the cells. Two regions of the chromatogram from the Sephacryl column exhibited anti-proliferative activity, one corresponding to higher molecular weight species (typically tubes 40-60), and another corresponding to lower molecular weight species (at about tubes 100-110).

The higher molecular weight active fractions from the gel filtration column were pooled, dialyzed to remove salt and lyophilized to concentrate. The material was applied to an HPLC-DEAE ion exchange column and eluted with a linear gradient of 0-1M NaCl. All of the biologically active material eluted in the early part of the chromatogram corresponding to material that did not absorb to the resin. Considerable protein was retained on the column thus affording significant purification of the active embryonal factor.

After dialysis versus water to remove salts followed by lyophilization, the active fractions from the DEAE peak were subjected to mass spectrometry on a PerSeptive Biosystems Voyager Elite MALDI-TOF mass spectrometer. Only a few peaks were seen from the pooled active fractions, including major components with molecular masses of 10821, 14832 and 14987 Da. Several smaller peaks were found at 5411 and 7477 Da. No peaks were found at higher or lower molecular masses. This finding suggests a considerable purification of the active material.

The low molecular weight fractions from the gel filtration column were pooled and lyophilized. They were reconstituted in water and applied to C18 reversed-phase HPLC column. Buffer A was 0.1% trifluoroacetic acid in water; buffer B was 0.1% trifluoroacetic acid in 99.9% acetonitrile. The column was developed with a linear gradient of 0-100% buffer B over 1 hour. Fractions were collected and tested for biological activity in the MCF-7 assay. Activity appeared to be spread out over fractions 10-20, and very little protein was seen on the chromatogram within this area.

After concentration of the pooled fractions, mass spectra revealed an approximately 820 Da peptide that was present in all of the active fractions from the reverse phase column and absent from the non-active regions of the column. Experiments were performed to determine its structure by performing a controlled proteolytic digestion using carboxypeptidase Y and analyzing the progressive fragmentation of the peptide by mas spectrometry. Although there appeared to be some heterogeneity in the proteolytic fragment, it was possible to fit the spectra with the following heptameric polypeptides.

NH$_2$-Cys-Val-His-(Ala, Ser, Thr)-(Tyr, Phe)-Arg-(Ser-Ala)-COOH

This peptide in all of its combinations was synthesized by manual SSPS using Fmoc (9-fluorenylmethoxycarbonyl) as the amino-terminal protecting groups. At each position where more than one amino acid was possible, a mixture of the putative amino acids was added to the nascent peptide to produce a final product containing all possible combinations.

This combinatorial mixture, when tested by measuring the uptake of radiolabeled thymidine by MCF-7 cells in culture, exhibited no inhibitory activity. It is likely that this lack of effect results from the fact that the peptide mixture consists of peptide analogs with high sequence homology some of which may be able to compete with active peptides for receptor sites on the MCF-7 cells but not possess biological activity. Accordingly, the peptide mixture was then separated by reversed-phase HPLC (FIG. 8) and the individual peptides (A-M) were collected dried by vacuum centrifugation (Speed Vac) and separately tested in duplication the MCF-7 assay (FIG. 9). Peaks A, F and K exhibited substantial antiproliferative activity when compared to a negative control (buffer alone) whereas the other peptides were less active or showed no activity. Peptides A, F and K all possessed molecular masses of 818.6 kDa which has been calculated to correspond to the following sequences:

```
                                          (SEQ. I.D. NO:3)
              NH2-Cys-Val-His-Ala-Phe-Arg-Ser-COOH (SEQ. I.D. NO:2)
              NH2-Cys-Val-His-Ala-Tyr-Arg-Ala-COOH (SEQ. I.D. NO:8)
              NH2-Cys-Val-His-Ser-Phe-Arg-Ala-COOH
```

What is claimed is:

1. An isolated peptide selected from the group consisting of:

Cys Val His Ala Tyr Arg Ala;    (SEQ ID NO:2)

Cys Val His Ala Phe Arg Ser; and    (SEQ ID NO:3)

Cys Val His Ser Phe Arg Ala.    (SEQ ID NO:8)

2. An isolated peptide consisting of Cys Val His Ala Tyr Arg Ala (SEQ ID NO:2).

3. An isolated peptide consisting of Cys Val His Ala Phe Arg Ser (SEQ ID NO:3).

4. An isolated peptide consisting of Cys Val His Ser Phe Arg Ala (SEQ ID NO:8).

5. A composition comprising an excipient and at least one isolated peptide consisting essentially of:

Cys Val His Ala Tyr Arg Ala;    (SEQ ID NO:2)

Cys Val His Ala Phe Arg Ser; or    (SEQ ID NO:3)

Cys Val His Ser Phe Arg Ala.    (SEQ ID NO:8)

6. A composition consisting essentially of an isolated peptide selected from the group consisting of:

Cys Val His Ala Tyr Arg Ala    (SEQ ID NO:2);

Cys Val His Ala Phe Arg Ser    (SEQ ID NO:3); and

Cys Val His Ser Phe Arg Ala    (SEQ ID NO:8).

* * * * *

SEQUENCE LISTING

```
<160> NUMBER OF SEQ ID NOS: 12

<210> SEQ ID NO 1
<211> LENGTH: 7
<212> TYPE: PRT
<213> ORGANISM: sos scrofus (pig)

<400> SEQUENCE: 1

Cys Val His Ala Tyr Arg Ser
1               5

<210> SEQ ID NO 2
<211> LENGTH: 7
<212> TYPE: PRT
<213> ORGANISM: sos scrofus (pig)

<400> SEQUENCE: 2

Cys Val His Ala Tyr Arg Ala
1               5
```

```
<210> SEQ ID NO 3
<211> LENGTH: 7
<212> TYPE: PRT
<213> ORGANISM: sos scrofus (pig)

<400> SEQUENCE: 3

Cys Val His Ala Phe Arg Ser
1               5

<210> SEQ ID NO 4
<211> LENGTH: 7
<212> TYPE: PRT
<213> ORGANISM: sos scrofus (pig)

<400> SEQUENCE: 4

Cys Val His Ala Phe Arg Ala
1               5

<210> SEQ ID NO 5
<211> LENGTH: 7
<212> TYPE: PRT
<213> ORGANISM: sos scrofus (pig)

<400> SEQUENCE: 5

Cys Val His Ser Tyr Arg Ser
1               5

<210> SEQ ID NO 6
<211> LENGTH: 7
<212> TYPE: PRT
<213> ORGANISM: sos scrofus (pig)

<400> SEQUENCE: 6

Cys Val His Ser Tyr Arg Ala
1               5

<210> SEQ ID NO 7
<211> LENGTH: 7
<212> TYPE: PRT
<213> ORGANISM: sos scrofus (pig)

<400> SEQUENCE: 7

Cys Val His Ser Phe Arg Ser
1               5

<210> SEQ ID NO 8
<211> LENGTH: 7
<212> TYPE: PRT
<213> ORGANISM: sos scrofus (pig)

<400> SEQUENCE: 8

Cys Val His Ser Phe Arg Ala
1               5

<210> SEQ ID NO 9
<211> LENGTH: 7
<212> TYPE: PRT
<213> ORGANISM: sos scrofus (pig)

<400> SEQUENCE: 9

Cys Val His Thr Tyr Arg Ser
1               5
```

-continued

```
<210> SEQ ID NO 10
<211> LENGTH: 7
<212> TYPE: PRT
<213> ORGANISM: sos scrofus (pig)

<400> SEQUENCE: 10

Cys Val His Thr Tyr Arg Ala
 1               5

<210> SEQ ID NO 11
<211> LENGTH: 7
<212> TYPE: PRT
<213> ORGANISM: sos scrofus (pig)

<400> SEQUENCE: 11

Cys Val His Thr Phe Arg Ser
 1               5

<210> SEQ ID NO 12
<211> LENGTH: 7
<212> TYPE: PRT
<213> ORGANISM: sos scrofus (pig)

<400> SEQUENCE: 12

Cys Val His Thr Phe Arg Ala
 1               5
```